(12) United States Patent
Loppacher et al.

(10) Patent No.: US 9,383,377 B2
(45) Date of Patent: Jul. 5, 2016

(54) METHOD AND DEVICE FOR AUTOMATICALLY DETECTING SUBSTANCES FOR ANALYSES

(75) Inventors: Matthias Loppacher, Basel (CH); Manuel Altmeyer, Rapperswil (CH); Christoph Fankhauser, Bubendorf (CH); Urs Schranz, Arlesheim (CH)

(73) Assignee: CAMAG, Muttenz (CH)

( * ) Notice: Subject to any disclaimer, the term of this patent is extended or adjusted under 35 U.S.C. 154(b) by 423 days.

(21) Appl. No.: 13/989,831

(22) PCT Filed: Nov. 21, 2011

(86) PCT No.: PCT/IB2011/055211
§ 371 (c)(1),
(2), (4) Date: May 28, 2013

(87) PCT Pub. No.: WO2012/073148
PCT Pub. Date: Jun. 7, 2012

(65) Prior Publication Data
US 2013/0239665 A1    Sep. 19, 2013

(30) Foreign Application Priority Data

Nov. 30, 2010   (CH) ..................................... 2007/10

(51) Int. Cl.
*G01N 1/00* (2006.01)
*G01N 35/10* (2006.01)
*G01N 35/00* (2006.01)
*G01N 1/40* (2006.01)
*G01N 30/00* (2006.01)
*G01N 30/06* (2006.01)

(52) U.S. Cl.
CPC ............ *G01N 35/10* (2013.01); *G01N 35/1095* (2013.01); *G01N 35/00029* (2013.01); *G01N 2001/4061* (2013.01); *G01N 2030/009* (2013.01); *G01N 2030/062* (2013.01)

(58) Field of Classification Search
CPC ........... G01N 1/38; G01N 1/405; G01N 1/10; B01L 2300/0816
USPC ....................................................... 73/61.59
See application file for complete search history.

(56) References Cited

U.S. PATENT DOCUMENTS

2007/0255506 A1* 11/2007 Lobban et al. .................. 702/19

* cited by examiner

*Primary Examiner* — Hezron E Williams
*Assistant Examiner* — Rodney T Frank
(74) *Attorney, Agent, or Firm* — Buchanan Ingersoll & Rooney PC (57) ABSTRACT

A fully automatic extraction and analysis system for biologically active samples significantly simplifies the analysis of, for example, DMS samples and has significant advantages over the manual technology and the partially automated technology (punching out). The described extraction system is the first economical alternative to conventional blood analysis and supports the spread of said time-, cost-, and animal-saving technology in pharmacology and toxicology.

21 Claims, 6 Drawing Sheets

METHOD AND DEVICE FOR AUTOMATICALLY DETECTING SUBSTANCES FOR ANALYSES

The present invention relates to a method and device for automatically detecting substances for analyses.

In the development of medicines, the screening of large quantities of blood samples is an indispensable test method and, through the demands of the regulatory authorities, an absolute requirement. In recent years, the analysis of dried blood spots (DBS) has attracted attention on account of the considerable advantages of these over conventional blood samples. In particular, the significant reduction in the required volume of blood and the easier shipment and storage lead to a considerable saving in terms of the overall costs of blood analyses.

In addition, the smaller amount of blood needed means that far fewer test animals have to be used, which is consistent with the three Rs concerning animal tests (replacement, reduction, refinement). For DBS analyses, only 15 µl of blood are typically needed per measurement, the blood being applied to a filter paper (so-called DBS cards), dried, shipped, and analyzed in a central laboratory using a mass spectrometer (MS). Before the MS analysis, the blood sample has to be extracted from the DBS card. This presently requires considerable work, to the detriment of DBS technology, since this process has not hitherto been automated. The DBS analysis known today is time-consuming and expensive, and the advantages of this method have not yet been fully realized. Therefore, a fully automatic system for the extraction of DBS cards, with direct coupling to MS, is of very great interest for the blood analysis industry.

The method has proven useful and is nowadays similarly applied for other substance samples, e.g. bone marrow, cerebrospinal fluid, synovial fluid, sperm, stools, urine, blood plasma, etc., which are generally referred to as "Dried Matrix Spot (DMS)". Particularly in the case of dried biological samples that have been applied in droplet form, the known methods are complicated, time-consuming and, for some analyses, too rudimentary to ensure precise and reliable data. In order to transport the samples and, for example, to supply them in test tubes to the measuring equipment, these samples normally have to be present in solution, in emulsion or in dilute mixture. Such samples contain relatively small fractions of the desired substances that are to be assessed. Particularly in drug screening or in doping tests, but in all other routine examinations too, it would be desirable to measure as far as possible only the desired substances, in as durable a form as possible, similarly to the DBS samples described above, in order to be able to carry out precise measurements in a short space of time and to keep expenditure on transport and storage to a minimum. Such samples can be stored in a manner that saves space and can be analyzed at a later time.

Swiss patent application CH-01166/09 proposes a method, and the associated device, for the detection of liquid samples, highly viscous samples, dried samples, coagulated or thickened samples, samples present in solid form, dried-in and biologically active samples, or samples to which protective colloids are added for stabilization. The device and method are also suitable for the analysis of microscopy sections, which contain substances in corresponding concentrations. In this way, even small amounts and concentrations of the substances to be tested are analyzed reliably and precisely.

A problem of the methods to date lies in practice in the large number of the samples which are to be analyzed, which have to be analyzed within a short time. Laboratories simply do not have the time needed to analyze sufficient samples to be able, subsequently, to present meaningful statistics. In clinical tests in particular, a large number of samples would have to be measured in order to obtain statistical values and in order, on the basis of these values, to be able to draw conclusions with any certainty.

Figure 1:
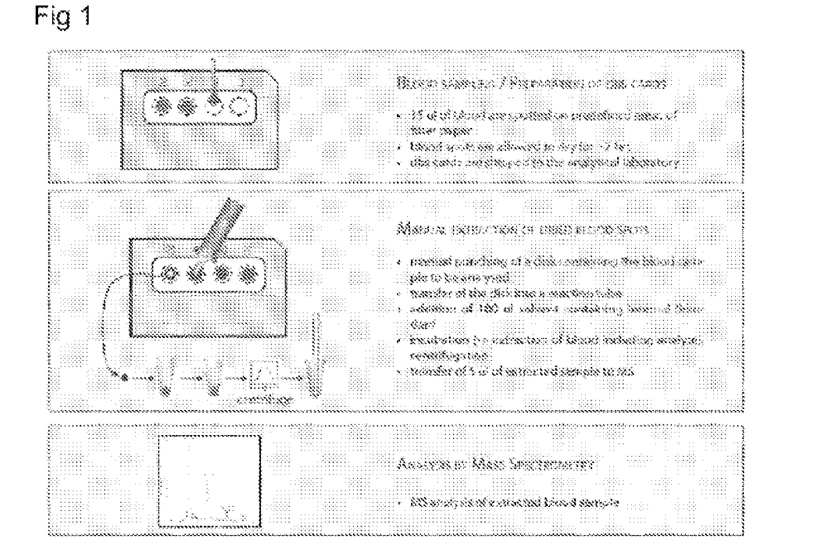
FIG. 1 shows a systematic representation of a manual method.

As is shown schematically in FIG. 1, the punching-out of DBS disks is nowadays carried out manually. Since the method is manually difficult and the effort needed takes up too much time, this procedure and method has not yet really caught on. As a result of the growing interest in DBS technology, automatic punchers were introduced (BSD robotics, Perker Elmer). The method proposed here for DBS is also used successfully for DMS. These systems automatically punch out a disk, for example of 3.2 mm in diameter, from a DBS card into a small glass vessel (vial). The extraction agent must then be added, and the sample must be treated by an agitator or ultrasound, for the purpose of better extractability, and thereafter delivered to MS. The time-consuming nature of the method may be the reason why only a few groups have hitherto reported an online extraction of DBS cards.

Other techniques, such as punching out the disks and packing them in cartridges with subsequent extraction or "desorption electrospray ionization" (DESI), have been tested by the industry, but none of the techniques has the corresponding sensitivity or simplicity that is sought and needed.

Despite the growing interest shown by pharmaceutical multinationals in DBS technology, there is at present no fully automatic system available in which the user can transfer the DBS cards, without further interaction, to the system for reliable and precise analysis.

The object of the present invention is now to improve an automated method and a device for automatic detection of samples, typically consisting of a matrix, e.g. blood, and other substances, for analyses of the type mentioned at the outset, and to do so in such a way that, while the advantages of known methods and devices are maintained, it is possible for a large number of samples to be processed, and their data detected, quickly and without manual work.

The figures depict possible illustrative embodiments, which are explained in the description below.

Figure 2:
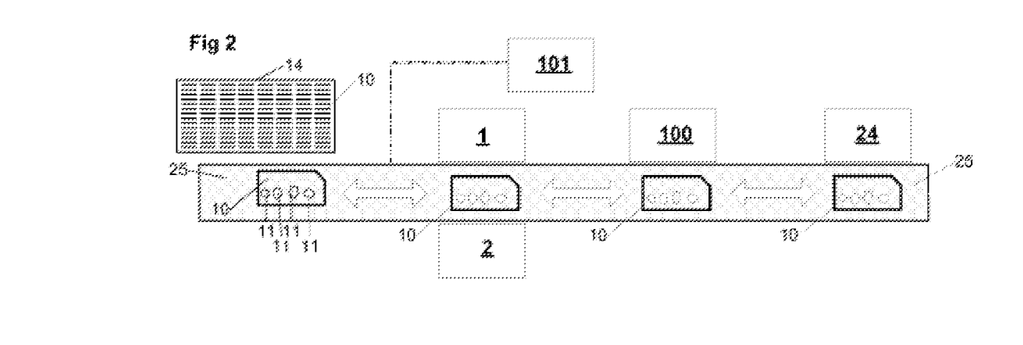
FIG. 2 shows a systematic representation of an automated method.
Figure 3:
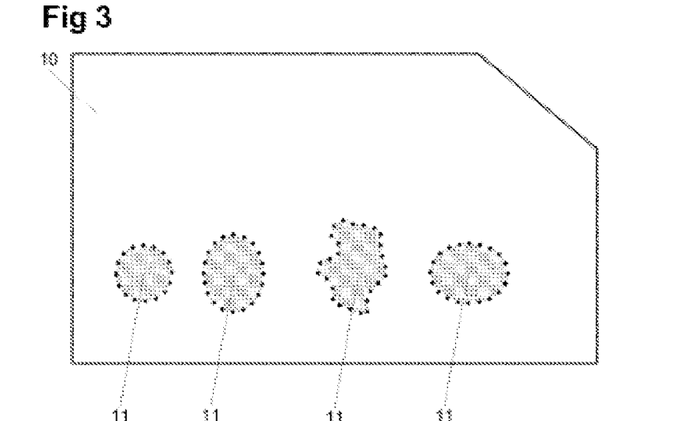
FIG. 3 shows a plate with samples.
Figure 4:
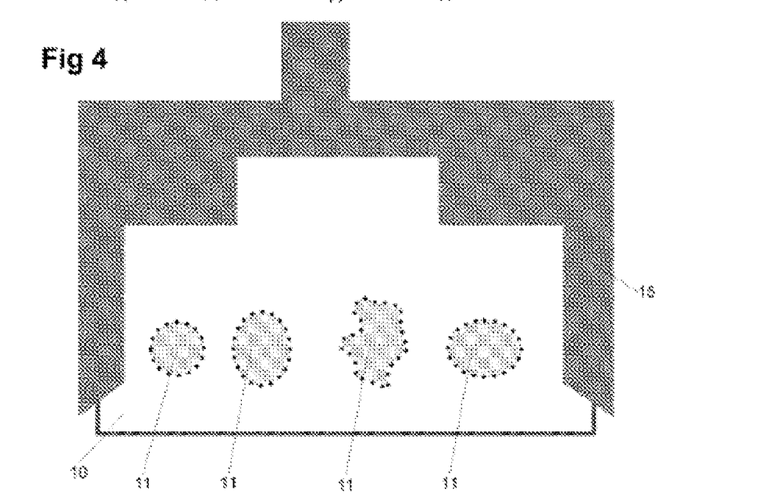
FIG. 4 shows a view of a gripper with plate.

A robotic system, here called robot 25 for short and shown schematically in FIG. 2, is equipped for handling the DMS cards with a newly developed gripper 15, which is suitable for the automation and which takes a plate 10 from the magazine 14 and transfers it to an extraction head 1/counterpart extraction head 2, a measuring head 100 for optical detection of the DMS cards, and to the applicator head 24, which permits time-saving, reliable and reproducible analysis of several hundred DMS cards in a short time without human interaction.

A possible system looks as follows: Plates 10 are stored in one or more racks of a magazine 14 (FIG. 2). One possible embodiment corresponds more or less to a system as was previously used for the storage of slides for analog projection. However, in view of the strict demands in terms of reliability, the transport systems that were used for the slide projection are far too unreliable and, in addition, only permit transport to a station outside the racks. With such systems, bent cardboard frames permitted only inadequate reliability. The racks were therefore optimized such that the plates corresponding to the slides are not pushed out, but instead are gripped on one or more sides, ideally on three sides, by a specially developed gripper 15. The robot 25 guides the gripper 15, which holds the plates 10 firmly and flat and, when required, guides them to and away from the stations represented by measuring head 100, extraction head 1/counterpart extraction head 2, and applicator head 24 (FIG. 2).

One embodiment of the racks provides a multiple guide, e.g. to the left and right, wherein outside this guide, in the outer area of the frame of the plates 10, there is sufficient space for secure gripping of the plates 10. The described embodiment represents only one possible variant. Gripping with the specially developed gripper is not only punctiform but instead also takes place at least on a line or elongate surface and additionally by means of a special pattern, e.g. ribs, tips or generally elevations, which are arranged on the gripper in a partial area. The plates are thus firmly fixed, on the one hand, by the elevations in a partial area and, on the other hand, are guided by the lines or elongate surfaces. The gripper thus performs two clear functions:

The guiding, which is enormously important for plates 10 which are not dimensionally stiff and flat. Such plates 10 are brought into and kept in a plane and flat state by the guiding of the gripper 15. Flat and plane plates 10, or plates 10 held flat, can be more reliably and easily processed in the subsequent stations.

The fixing, which has to hold the plates 10 absolutely steady, is important for the reliable function of the robot 25. It is an absolutely essential condition to ensure that the plates, from being removed from the rack by the robot 25 to being returned to the rack, are held securely in the gripper, and to position the plates precisely at the individual stations. For this purpose, ribs, tips or other kinds of elevations 16 of the gripper 15 (FIG. 5) penetrate into the surface of the plates 10.

Known gripper systems have known drawbacks in terms of guiding and/or fixing. For this reason, when developing the gripper 15 proposed here, special attention was paid to the guiding and fixing of the plates 10.

The measuring head 100 analyses the optical properties of the plate. A simple embodiment is a punctiform optical sensor, which detects optical properties, shape and position of the sample 11. It also measures the brightness of the sample 11 as a whole or at many points, absorption and fluorescence, applied markings and bar codes, and forwards these to a microprocessor 101 for further analysis and calculation of parameters. Generally, a digital camera is used, which can perform all of these functions. A more efficient variant involves the use of a digital camera with integrated evaluation electronics, a so-called smartcam, which makes it possible to calculate these parameters directly in the camera and forward them to the microprocessor 101 or to a further processing system. It has been shown that the position and shape of the samples on the plate 10, the brightness and the homogeneity of the brightness are of crucial importance. On the one hand, there are acceptance criteria for the samples 11 on the plate 10, and, on the other hand, it is important that extraction head 1 and counterpart extraction head 2 are applied at the center of the sample 11. The automation of these steps affords great advantages over manual methods, since the positioning guided by the robot 25 and controlled by the measuring head 100 is much more precise and reliable. Many measurement errors that can occur in the manual method are thereby avoided. For example, if the sample 11 were met only partially or at the edge, this would result in a measurement value that is too small or distorted, which can have fatal consequences, particularly in the development of medicines. The measuring head supplies the robot with the exact positional data of the samples 11, which permits a precise orientation of the extraction head 1 and counterpart extraction head 2 with respect to a sample 11 on the plate 10 and guarantees more reliable measurement data.

Moreover, the measuring head 100 can perform the following tasks: Reading-in of bar codes for the verification of the sample identity, identification of, for example, crossed-off check boxes on the plate 10, which indicate the spots as non-usable or even reject. All optically detectable markings, including text, can be detected per se. If a smartcam is used as measuring head 100, the data can be evaluated directly. If a simple measuring head 100 is used, the raw data are delivered to the microprocessor 101, which evaluates them and sends corresponding signals to the robot 25. If a simple measuring head 100 is used which measures without surface optical detection, e.g. a point or bar code sensor, the plate 10 with the sample 11 is moved relative to the measuring head 100 for a large number of measurements. The measurements are then brought together numerically by the microprocessor 101 to give an overall figure, such that the corresponding information can be derived from the calculated overall figure. It is possible to bring the measuring head 100 to the plates 10 with the samples 11 or, by means of the robot 25, to bring the plates 10 with the samples 11 to the measuring head. Depending on the possibilities of the robot 25, it is possible to do without a movement of the measuring head 100.

After the microprocessor 101 has received from the measuring head 100 the input for the exact desired position of the sample 11 relative to the extraction head 1 and counterpart extraction head 2, the plate 10 with the sample 11, the extraction head 1 and the counterpart extraction head 2 are optimally oriented with respect to one another by means of the robot 25 and/or the movement of the extraction head. In the state when brought together, extraction head 1 and counterpart extraction head 2 now isolate an area of the sample 11.

Figure 5:
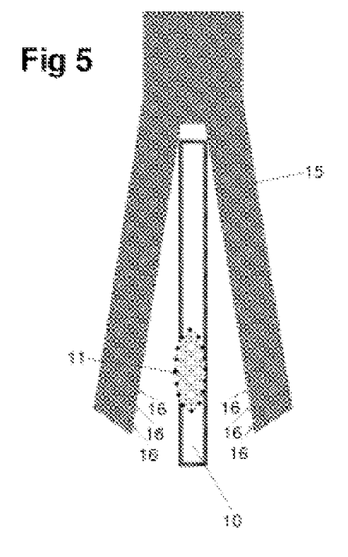
FIG. 5 shows a side view of a gripper.

Tests have shown that it may be advantageous if extraction head 1 and counterpart extraction head 2 are guided together to a controlled distance and do not completely clamp plate 10 and sample 11 by means of pressure up to the corresponding counter-pressure (FIG. 5). This should and will prevent the punching-out of the sample 11 on the plate 10. Extraction head 1 and counterpart extraction head 2 can be brought together in a controlled manner, for example using an abutment, or using the precise robot 25 guided and controlled by the microprocessor 101.

If the sample 11 is now positioned between extraction head 1 and counterpart extraction head 2 (FIG. 6), liquid that arrives via an admission line 8 and leaves via a discharge line 9 flows as homogeneously as possible through the sample. Optimally, the flow of liquid through the sample 11 additionally takes place by the longest possible path. An arrangement in which admission line 8 and discharge line 9 are as far away from each other as possible, or in which an admission line 8 is present on the extraction head 1 and a discharge line 9 on the counterpart extraction head 2 (through the sample 11), are good solutions, and the combination of both measures represents the preferred solution.

A so-called DMS-MS (Dried Matrix Spot Mass Spectrometer) system is used for the analysis. That is to say, the extract of the Dried Matrix Spots (DMS) is forwarded to a mass spectrometer (MS). The advantages of the fully automatic DMS-MS system are the following:

No time-consuming manual processes.

Fewer incorrect measurements as a result of errors by personnel.

Online extractions with small volume (concentrated samples).

Improved detection sensitivity (measurement of lower concentrations possible).

System with sample identification (bar code reader).

Rapid and simple extraction directly into the mass spectrometer.

Smaller amounts of expensive internal standard needed.

The fully automatic method with the DMS-MS extraction system forms the basis of the invention and will significantly simplify the analysis of DMS samples, and it also has significant advantages over the manual technology and the partially automated technology (punching out).

The described extraction system is the first economical alternative to conventional blood analysis and will support the spread of this time-saving, cost-saving and animal-saving technology in pharmacology and toxicology.

Figure 6:
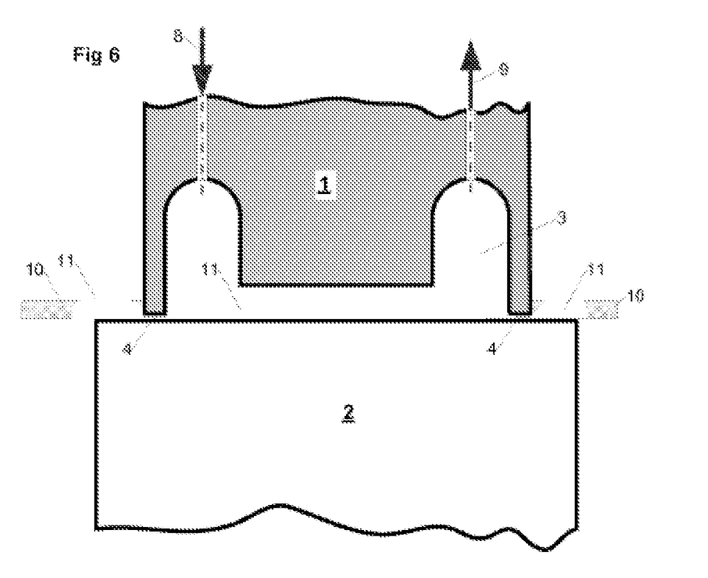
FIG. 6 shows an extraction head, sample, and counter-part extraction head.

Clamping and Sealing Process (FIG. 6):

The sample 11 located on the plate 10 is clamped between extraction head 1 and counterpart extraction head 2. By the compression of the area of the sample 11 on and in the plate 10 in the area where the sealing edge 4 comes to lie, a leak tight and inherently closed sealing line is provided for liquids, and preferably also for gases, as a result of which the sample 11 is spatially tightly enclosed by the extraction head 1 and counterpart extraction head 2 except for admission line 8 and discharge line 9. Depending on the properties such as hardness, density, elasticity and ductility of the sample 11 and of the plate 10, the stated compression of the thickness in the area of the sealing line can only be reduced to a small degree from 100% to e.g. 50%, to a high degree from e.g. 100% to 10% of the original thickness or even to practically 0%, whereby only very small amounts of the material of sample 11 and plate 10 are located in the area of the sealing line between extraction head 1 and counterpart extraction head 2. It has been found that the compression must be optimized experimentally depending on the required compressive strength.

Plates & Sample

The plates 10 often consist of filter papers, for example, on which the samples 11, e.g. in an approximate diameter of ca. 7 mm, form a spot passing through the paper (e.g. DBS: dried blood spots; DPS: dried plasma spots; DUS: dried urine spots; or generally DMS: Dried Matrix Spots for dried spots of any liquids). Dried-in samples 11 of blood droplets, blood plasma droplets or urine droplets can be enclosed by said sealing line in this case, e.g. with a 4 mm circle, which is ideally chosen in the center of the spot. However, this is not important in every case, but the analysis in the measuring head provides information on where the best sample 11 is located and controls the installation precisely there via the robot 25. However, it is possible in practice to use all forms of spots. The size of the spots and of the surface enclosed by the sealing line can also vary depending on the application, for example <1 mm extent to >10 mm for thicknesses of the plate 10 of 0.5 mm, for example. The ratio of the surface enclosed by the diameter from the sealing line to the thickness of the plate 10 is, however, greater than 0.5, preferably greater than 1, wherein no limits are set by the process to greater ratios of over 100. Trials have shown that very good and reproducible results are achieved in the range of 2 to 10, which for example with a thickness of 0.5 mm, and in the case of a circular sealing line, corresponds to a diameter of 1 to 5 mm.

Blood spots are just one of many possibilities of how a sample of this kind could look. As plate 10, it is possible to use a very wide variety of materials, but these materials are ideally compressible, and the sample 11 can be at least partially sucked up. As sample 11 in bioanalysis, for example, blood, blood plasma, urine or all other conceivable biological liquids are applied to plates 10 and dried. In the case mentioned, the drying is used for conservation, which makes it possible to store and transport these biological samples without cooling and to analyze them only after a number of days, weeks or even months have passed, without this impairing the analysis, wherein the maximum storage period naturally depends on the sample used.

Extraction Process

The sample 11 on the plate 10 (FIG. 6) is enclosed tightly in the cavity 3 between extraction head 1 and counterpart extraction head 2, except for admission line 8 and discharge line 9, and a liquid, which is introduced through the admission line 8, now flows at least partially through the sample 11. Parts of the sample 11 and, if appropriate, also parts of the plate 10 are washed out. Thereafter, the liquid, together with these washed-out parts, leaves the cavity 3 through the discharge line 9. Instead of the liquid, it is equally possible to use a gas, saturated vapor, a combination of the two, or any desired non-solid medium which is suitable for extracting those parts of the sample 11 that are of interest. It may also be advantageous to use a medium that changes over time, which, in the case of solvents, corresponds to a changing mixture, a so-called gradient. For example, if the sample is sparingly soluble, the extraction conditions can be adapted: Very slowly or via many rapid short movements, followed by wait times, or with elevated temperature, which make it possible to free more of the desired substances from the sample 11, which, in the sense of analysis, increases the efficiency of the extraction and ultimately the recovery.

Forwarding of the Extract

The medium, which contains parts of the sample 11 and possibly of the plate 10, is now forwarded through the discharge line 9; it is called extract. This extract ideally has the parts of the sample 11 that are of interest in terms of analysis (desired substances), wherein the extract can always contain one or more substances. Other parts of the sample 11 or of the plate 10 that are themselves unnecessary and cause interference (matrix) should be reduced to the minimum. This extract is now gradually pushed forward by new medium that is introduced through the admission line 8 into the cavity and that leaves the latter again via the discharge line 9. The extract can have a non-homogeneous composition, on the one hand by means of the medium that flows first through the admission line 8 and the sample 11 having a different composition than the medium that subsequently flows through these, and also by means of a varying concentration of the desired substances. At the outset, a rising concentration is usually established (run-up), which is followed by the desired concentration, which in turn transitions into a falling concentration (run-down).

One possibility now is for the extract of each sample to be filled into one or more vials. Typically, one vial per sample is filled with the corresponding extract, and the vials, in racks of 96 vials for example, are transferred onward for further processing to customary autosamplers for analysis with other subsequent methods, e.g. HPLC, HPLC-MS, HPLC-MS-MS, direct MS or MS-MS, GC, NMR or other suitable analytical methods.

A further possibility is that the extract is transported onward via a valve into a container or storage vessel, which can be a capillary for example, and, after this valve has been switched, is conveyed back out of this storage vessel and forwarded directly to the subsequent station, e.g. by a capillary which is connected directly to the subsequent analytical apparatus. Depending on the concentration of the desired substances, the problem now arises that the concentration is too low for the subsequent method or may also be too high. In the first case, the extraction conditions have to be optimized, and in the second case a dilution is necessary.

Dilution

If, for the subsequent method, the extract has too high a concentration of the desired substances, it has to be diluted. However, since matrix is also present in the extract, a dilution with pure medium represents only an inadequate solution to the problem. Ideally, for example, an extract diluted by 1:10 would, with the same overall quantity, need to contain a tenth of the desired substances and the same amount of matrix and any other substances as an undiluted sample. This is important, since the matrix often greatly influences the measurement behavior in the subsequent methods. In this case, therefore, only one tenth of the extract of the sample 11 to be analyzed would have to be mixed with nine tenths of a sample that contains all the substances of the matrix but nothing of the desired substance, a so-called blank sample.

This can be illustrated using the example of coffee extraction from caffeine-containing coffee (CAF) and decaffeinated coffee (DECAF). Coffee, like our samples, is generally extracted by a liquid flowing through it. Very strong coffee is obtained at the start of the extraction, gradually thereafter increasingly weaker coffee, which, at normal amounts of coffee, corresponds to a moderately concentrated normal coffee (NORM) in a coffee cup and, at small amounts, corresponds to a highly concentrated ristretto (RIST) in what is, for example, a ten times smaller ristretto cup. If we now wish to determine the caffeine content of a NORM CAF in a coffee cup, but our method of analysis is so sensitive that it already reaches saturation at this concentration of coffee, we cannot simply dilute a RIST CAF with water to a coffee cup amount, since this dilution would have a completely different composition than the NORM CAF and the measurement would also have very different results. We would have to mix one cup of NORM CAF with nine cups of NORM DECAF and remove one cup and measure the caffeine concentration therein. We would therefore require a total of ten cups of coffee, which would be too large an amount for the measurement. However, if we were to remove one tenth from a cup of NORM CAF (substance, i.e. caffeine plus matrix) and nine tenths from a cup of NORM DECAF (only matrix) and mix them together in a third cup, this works. Assuming, of course, that the coffee is present homogeneously in the cups.

The homogeneous mixing is the problem in our described extraction of the sample 11, since the extract is usually conveyed through lines (very thin capillaries) and it does not automatically mix homogeneously, such that we also cannot easily remove a representative tenth of the extract of the sample and nine tenths of the extract of the blank sample. As with the coffee, therefore, before the tenth is removed, a mixing of the entire extraction of the sample 11 has to take place, ideally also before the removal of the nine tenths of the blank sample. If a dilution to a hundredth is desired, the mixing of the blank sample is no longer of such great importance, since in any case the entire extract of the blank sample is used except for one percent, and it can therefore be ignored. However, the homogeneous mixing of the extract of the sample 11 then assumes very great importance, since only one percent of this is used.

We therefore fill a first extraction of a blank sample into a first storage vessel, mix the entire content of the first storage vessel homogeneously, e.g. with a magnetic stirrer built into the storage vessel, then fill a second extraction of a sample 11 into a second storage vessel, mix the entire content of the second storage vessel homogeneously, then remove nine tenths from the first storage vessel and one tenth from the second storage vessel, bring this tenth and the nine tenths together, and analyze the whole. The whole can once again be mixed, unless the subsequent analysis automatically compensates for this and renders it unnecessary.

It is equally possible to fill a first extraction into a first storage vessel and mix it, transfer nine tenths therefrom into a second storage vessel and then fill a second extraction into this first storage vessel and mix it, remove a tenth and transfer it into a third storage vessel, and then convey the content of the second and third storage vessels together to the subsequent analysis method, wherein the second and third storage vessels can also be combined in one storage vessel. If the second and third storage vessels are not combined, the mixing ratio can also be generated by removing suitable amounts from the second and third storage vessels. The whole can be mixed again, unless the subsequent analysis automatically compensates for this. With this method, any desired dilution ratio can be achieved while maintaining the desired total quantity.

Going back to the example of coffee extraction from caffeine-containing coffee (CAF) and decaffeinated coffee (DECAF): Instead of whole cups of coffee of the types DECAF and CAF, which are brought together after the extraction such that a suitably diluted caffeine concentration is obtained in the resulting cup, another very interesting variant of this result can be achieved directly. Let us assume, for the sake of simplicity, that a coffee extraction takes one hundred seconds. In the extraction of CAF, we proceed as follows: Every ten seconds we hold a first empty cup, always for just one second, under the coffee machine and thus collect in ten times a second only one tenth of the coffee of the type CAF, the rest goes into the collecting tray and is lost, after which comes the extraction of the DECAF, where we hold a second cup for nine seconds every ten seconds under the coffee machine and thus collect, in ten times nine seconds, nine tenths of the coffee of the type DECAF; the contents of the first and second cups are then brought together and can be measured. If the first cup is used once again as the second cup, the bringing together is not needed. If necessary, the resulting coffee cup with the ten times lower concentration of caffeine can be stirred again, i.e. mixed, before the measurement. By means of suitable time intervals, it is possible to achieve every desired caffeine content of the coffee of the resulting cup.

The possibility, described with reference to coffee, of achieving any desired dilution of a sample 11 is referred to as chopping the extract. For example, if 100 µl are extracted over a time of 100 seconds, it is possible to proceed as follows: Of the extraction of the blank sample, the µl 1-4, 6-14, 16-24, 26-34, 36-44, 46-54, 56-64, 66-74, 76-84, 86-94, 96-100 are filled into the first storage vessel, and the µl 5, 15, 25, 35, 45, 55, 65, 75, 85, 95 are discarded, such that the first storage vessel is filled with 90 µl. Of the extraction of the sample 11, the following µl are filled into the second storage vessel during the extraction: µl 5, 15, 25, 35, 45, 55, 65, 75, 85, 95, and the µl 1-4, 6-14, 16-24, 26-34, 36-44, 46-54, 56-64, 66-74, 76-84, 86-94, 96-100 are discarded. In this way, 90 µl of the extraction of the blank sample are in the first storage vessel, and 10 µl of the extraction of the sample are in the second storage vessel. As a result of the chopping of the 100 µl, the second storage vessel also contains, in its 10 µl, a representative extraction profile of the original 100 µl extraction. It is advantageous for the first and second storage vessels not to be made much larger than is necessary for the volumes that are to be stored.

If the chopping is carried out with still more steps, the smaller volume of the sample 11 corresponds more precisely to a part from the entire extraction profile of 100 µl. By chopping with a ratio other than 1 µl to 9 µl, a sample 11 can be diluted with a blank sample in any desired volume ratio, wherein the total volume can nevertheless be kept constant. The bringing together of the first and second storage vessels brings sample 11 and blank sample together again and permits the subsequent analysis of the diluted sample 11. It would be equally possible for the extract of the sample 11 to be filled not into the second storage vessel but instead directly into the first storage vessel behind the extract of the blank sample.

The described chopping thus permits any desired dilution of the sample 11 with blank sample while the quantity of overall extract is kept constant. In analysis, it happens again and again that samples 11 are present in excessively high concentrations and cannot be measured since, with such large measurement signals, the final analysis is saturated and delivers false results. With the described possibilities of dilution, this problem can be optimally solved, which is of great importance.

In the case of DBS samples in pharmacokinetics, the sample 11 consists of blood from a test subject who, for example, has ingested a medicament, wherein the traces of medicament in the blood are the desired substances, and of a blank sample which, except for the fact that the blood originates from a test subject who has not ingested a medicament and thus contains no traces of medicament, is otherwise identical to the sample 11.

Any remaining inhomogeneity, which arises when several storage vessels are washed out at time intervals one after another, can be easily compensated by a further mixer after the contents of the storage vessels have been brought together. Typically, only a passive mixer is needed here, which primarily mixes the flow of liquid by means of a vortex.

In the case of liquids, as is the case for example in HPLC, HPLC-MS, HPLC-MS-MS, MS or MS-MS, this is achieved by a first high-pressure pump which feeds the liquid into the admission line 8 of the extraction head 1 and then fills it as an extract into the storage vessels. From the storage vessel, the extract is looped into the liquid circulation of the subsequent methods and is conveyed onward by their delivery pumps to the analysis equipment. Matters are similar in the case of other media, except that, instead of high-pressure pumps, use is made of delivery systems for the corresponding media such as gases and vapors.

The fully automatic DMS-MS extraction system proposed here significantly simplifies the analysis of DMS samples and has significant advantages over the manual technology and the partially automated technology (punching out).

The described extraction system is the first economical alternative to conventional blood analysis and supports the spread of this time-saving, cost-saving and animal-saving technology in pharmacology and toxicology.

The installation with which this method is carried out consists of the parts that are specified in the preamble of claim 12. A large number of plates 10 are arranged in order in the magazine 14. Typically, plates consist of a more stable frame, which supports a flexible absorbing material. A common embodiment is a cardboard frame with a flexible, absorbing and highly absorptive material like a leaf. A more stable design of the frame can consist of correspondingly more durable material with a greater load-bearing capacity, e.g. plastic.

The measuring head 100 consists of an optical sensor, e.g. a point sensor. A more highly advanced design is a multi-point sensor or a digital camera (smartcam), which can contain an internal evaluation by means of a microprocessor 101 depending on the amounts of data, e.g. of the FPGA type. In addition, the measuring head 100 can be equipped with illumination, in order to be able to measure, independently of the ambient light, the optical properties of objects that are delivered to the measuring head 100.

The robot 25 has the task of moving and correctly positioning the plates 10 and the samples 11 according to claim 1, method steps a) to j).

Figure 7:
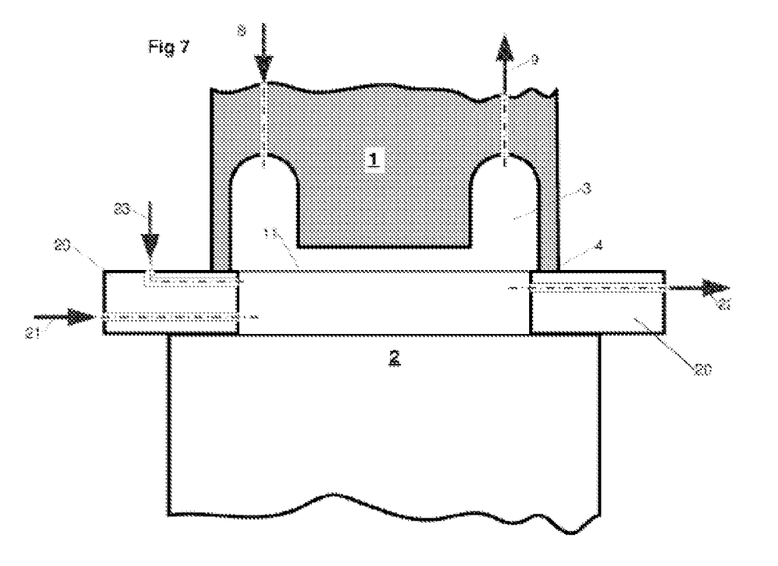
FIG. 7 shows a section through extraction head, wash unit, and counterpart extraction head.

The wash unit 20 (FIG. 7) is an additional part which is adapted to the shapes of the extraction head 1 and of the counterpart extraction head 2 and which is brought between extraction head 1 and counterpart extraction head 2 and, together with these, forms a closed or at least partially closed cavity. A washing liquid can be introduced into the cavity via the admission line 8, discharge line 9 or an inlet 21 of the wash unit 20. In order to completely empty the cavity after the cleaning process, gas is blown or sucked out of the cavity via a gas line 23 and the cavity is dried. In order to wash the extraction head 1 and the counterpart extraction head 2 clean, the media of the washing liquid are introduced into the cavity in a controlled manner, which can be done with high pressure, and they remain there for a desired period of time and are then blown out or sucked out by means of gas via discharge line 9 or outlet 22. The emptying of the cavity takes place via discharge line 9 or an outlet 22 provided in the wash unit 20. To provide support, residues of washing agent are sucked off via outlet 22, and the cavity between 1, 2 and 20 is dried, e.g. by inflowing gas. It can be advantageous if the wash unit is constructed such that it touches the extraction head 1 and the counterpart extraction head 2, arranged at some distance from each other, only outside the area in which they come into contact with the plate 10 and the sample 11. In this arrangement, the cavity 3, extended for the washing process, is sealed off by the wash unit 20 with respect to the extraction head 1 on the outside and the surface of the counterpart extraction head 2 (FIG. 6). This arrangement likewise permits the cleaning in the area of the sealing edge 4. The wash unit 20 is available as installation part and, when necessary, can be delivered by the robot 25 to the extraction head 1 and the counterpart extraction head 2.

The microprocessor 101 is the unit that controls the overall installation. Typically, an SPS or some other electronic component with a computing unit and firmware or software. There are connections to other components of the system.

The applicator head 24 is a system which applies an internal standard in liquid form to the sample 11. An internal standard is a reference substance which behaves very similarly to the substance and which can be clearly distinguished from the substance in the MS analysis. With the measurement of the internal standard, the absolute measurement intensity of the MS analysis can be calibrated if the quantity of the internal standard is known exactly. This can take place in liquid form, e.g. by means of spraying, atomizing, microdripping, processes from printing technology such as ink jet, pipe jet or electrical fields. The preferred process is spraying on with air, since the exact amounts applied can be done very precisely.

The invention claimed is:

1. A method for automatically detecting biological substances for analyses of samples applied to plates, wherein
- a) in a magazine, in which a large number of plates are stored,
- b) a gripper takes hold of a plate in the magazine in each case and delivers it to a measuring head for identification,
- c) the measuring head identifies the position and the shape of the samples by sensors,
- d) a microprocessor analyzes their position and shape,
- e) the relative orientation of an extraction head and of a counterpart extraction head with respect to the plate is adjusted by the microprocessor,
- f) the extraction head and the counterpart extraction head extract the desired substances from the sample,
- g) the measuring head checks optical properties of the sample for a correct processing sequence,
- h) the extraction head and the counterpart extraction head are cleaned of residues,
- i) the measuring head is brought together with the next sample,
- j) the sequence of the process from c) to i) is repeated with the new sample until all the desired samples on a plate are processed,
- k) the gripper returns the plate into the magazine,
- l) the procedure according to b) to k) is repeated until all the desired plates of a magazine are tested,
- m) after each extraction process according to f), the desired substances and matrix are forwarded for further processing.

2. The method as claimed in claim 1, wherein the measuring head detects an identification code present on the plate and establishes the sample identity.

3. The method as claimed in claim 1, wherein the desired substances and matrix extracted from a sample are stored in a container pending further processing and can subsequently be further processed using conventional autosamplers.

4. The method as claimed in claim 1, wherein the desired substances and matrix extracted from the sample are stored in a storage vessel pending further processing and can subsequently be forwarded to the further processing system.

5. The method as claimed in claim 1, wherein the desired substances and matrix extracted from the sample are temporarily absorbed in a "trapping column" pending further processing, and are subsequently freed again from this "trapping column" by another solvent and forwarded to the further processing system.

6. The method as claimed in claim 1, wherein the desired substances and matrix extracted from the sample are stored in a first storage vessel pending further processing, a further extraction according to f) from a blank sample is stored temporarily in at least one further storage vessel and, thereafter, the contents of the different storage vessels are brought together in such a ratio that the desired substances can be forwarded in diluted form and the matrix in undiluted form.

7. The method as claimed in claim 6, wherein the extractions from the sample and a blank sample are prepared, before being brought together, in such a way that, even when only a fraction of an extraction is used, this fraction represents an identical composition to the entire extraction from which it has been obtained.

8. The method as claimed in claim 1, wherein, after the identification of the samples according to c), an internal standard is applied to the sample as reference via an applicator head.

9. The method as claimed in claim 8, wherein the internal standard is sprayed on and at least partially penetrates the sample.

10. The method as claimed in claim 6, 7, 8 or 9, wherein at least two storage vessels of different size are used.

11. A device for automatically detecting biological substances for analyses of samples applied to plates comprising:
- a magazine for the plates;
- a gripper;
- a measuring head with an extraction head and with a counterpart extraction head;
- a microprocessor; and
- a robot wherein the extraction head with the counterpart extraction head and, lying between them, a plate with a sample form a cavity surrounded by a sealing edge, wherein this cavity is provided with an admission line and a discharge line, and the cavity, in a closed state, is surrounded by a sealing line which is defined by the sealing edge of the extraction head, the plate with the sample lying flat on the counterpart extraction head, such that the extraction head, the plate with the sample, and the counterpart extraction head, in the closed state when brought together, form a completely closed cavity isolated from the outside.

12. The device as claimed in claim 11, wherein the plates are arranged in the magazine.

13. The device as claimed in claim 11, wherein the plates are made of flexible absorbent material.

14. The device as claimed in claim 11, wherein the gripper grips and holds the plates at least along a substantial part of their long sides and guides and fixes them.

15. The device as claimed in claim 11, wherein the gripper grips and holds the plates at least along a substantial part of their broad sides and guides and fixes them.

16. The device as claimed in claim 11, wherein the gripper grips and holds the plates along a substantial part of their long and broad sides and guides and fixes them.

17. The device as claimed in claim 14, 15 or 16, wherein the gripper has structures which penetrate into the material on the surface of the plates and hold the plates flat.

18. The device as claimed in claim 11, wherein a wash unit has at least one of the following devices: an outlet, an inlet, and/or a feed.

19. The device as claimed in claim 11, wherein the measuring head has at least one of the following optical sensors: a spot position sensor, a brightness sensor, a contour sensor, a bar code recognition sensor.

20. The device as claimed in claim 19, wherein the measuring head has a sensor performing all functions.

21. The device as claimed in claim 11, wherein the distance between the extraction head and the counterpart extraction head, in the closed state, in the area of the sealing line of the sealing edge, has a precise distance greater than zero millimeters and smaller than half the plate thickness.

* * * * *